(12) United States Patent
Kochhar

(10) Patent No.: US 10,618,521 B2
(45) Date of Patent: Apr. 14, 2020

(54) WEARABLE IN-VEHICLE EYE GAZE DETECTION

(71) Applicant: Ford Global Technologies, LLC, Dearborn, MI (US)

(72) Inventor: Devinder Singh Kochhar, Ann Arbor, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 138 days.

(21) Appl. No.: 15/750,348

(22) PCT Filed: Sep. 20, 2015

(86) PCT No.: PCT/US2015/051168
§ 371 (c)(1),
(2) Date: Feb. 5, 2018

(87) PCT Pub. No.: WO2017/052493
PCT Pub. Date: Mar. 30, 2017

(65) Prior Publication Data
US 2018/0244279 A1 Aug. 30, 2018

(51) Int. Cl.
*B62D 6/00* (2006.01)
*B60W 40/08* (2012.01)
(Continued)

(52) U.S. Cl.
CPC ............ *B60W 40/08* (2013.01); *A61B 3/113* (2013.01); *A61B 5/0496* (2013.01);
(Continued)

(58) Field of Classification Search
CPC . G02F 1/29; G02F 1/134309; G02F 2001/294
(Continued)

(56) References Cited

U.S. PATENT DOCUMENTS 5,496,355 A  3/1996 Lipsky
5,726,916 A * 3/1998 Smyth ................. A61B 5/0496
                                              351/210
(Continued)

FOREIGN PATENT DOCUMENTS

WO     2014053534 A1    4/2014

OTHER PUBLICATIONS

Barea et al., "Sensory System for Implementing a Human-Computer Interface Based on Electrooculography", Sensors 2011, 11, 310-328; doi:10.3390/s110100310; ISSN 1424-8220.
(Continued)

*Primary Examiner* — Shardul D Patel
(74) *Attorney, Agent, or Firm* — Brandon Hicks; Bejin Bieneman PLC

(57) ABSTRACT

A system, including: one or more sensors included in an apparatus wearable by a vehicle operator to measure ocular muscle movement; and a computer that includes a processor and a memory, the memory storing instructions executable by the computer such that the computer is programmed to: receive data indicating ocular muscle movement from the wearable sensor; determine, using the measurement, a gaze direction of the operator; use the gaze direction to determine a level of operator attentiveness; and actuate a vehicle operation if the level of operator attentiveness is below a predetermined threshold.

20 Claims, 6 Drawing Sheets

(51) Int. Cl.
    *G08B 25/08*     (2006.01)
    *A61B 3/113*     (2006.01)
    *G08B 21/06*     (2006.01)
    *B60K 28/00*     (2006.01)
    *A61B 5/00*     (2006.01)
    *A61B 5/0496*     (2006.01)

(52) U.S. Cl.
    CPC ............ *A61B 5/6803* (2013.01); *B60K 28/00* (2013.01); *G08B 21/06* (2013.01); *G08B 25/08* (2013.01); *A61B 2503/22* (2013.01); *B60W 2040/0818* (2013.01); *B60W 2540/26* (2013.01); *B60W 2710/0605* (2013.01); *B60W 2710/18* (2013.01); *B60W 2710/20* (2013.01)

(58) Field of Classification Search
    USPC .................. 701/1, 41; 600/27, 300; 345/419
    See application file for complete search history.

(56) References Cited

U.S. PATENT DOCUMENTS

| | | | | |
|---|---|---|---|---|
| 6,226,570 | B1 * | 5/2001 | Hahn | B60K 28/066 |
| | | | | 701/1 |
| 6,542,081 | B2 | 4/2003 | Torch | |
| 7,204,250 | B1 | 4/2007 | Burton | |
| 8,690,750 | B2 * | 4/2014 | Krueger | A61M 21/00 |
| | | | | 600/27 |
| 9,794,475 | B1 * | 10/2017 | Tome | H04N 1/00129 |
| 2011/0176106 | A1 * | 7/2011 | Lewkowski | A61B 3/112 |
| | | | | 351/206 |
| 2013/0242262 | A1 * | 9/2013 | Lewis | G02B 27/0093 |
| | | | | 351/209 |
| 2014/0167957 | A1 * | 6/2014 | Tsuji | H04W 4/90 |
| | | | | 340/539.13 |
| 2014/0167967 | A1 * | 6/2014 | He | B60Q 9/00 |
| | | | | 340/576 |
| 2014/0184775 | A1 * | 7/2014 | Drake | A61B 3/14 |
| | | | | 348/78 |
| 2014/0194035 | A1 * | 7/2014 | Jourdian | A63H 18/02 |
| | | | | 446/446 |
| 2014/0195120 | A1 * | 7/2014 | McClain | G08G 1/16 |
| | | | | 701/41 |
| 2014/0289323 | A1 * | 9/2014 | Kutaragi | G06Q 50/01 |
| | | | | 709/203 |
| 2015/0025917 | A1 * | 1/2015 | Stempora | G06Q 40/08 |
| | | | | 705/4 |
| 2015/0185475 | A1 * | 7/2015 | Saarikko | G02B 6/02085 |
| | | | | 382/117 |
| 2016/0364881 | A1 * | 12/2016 | Mallinson | G06T 7/20 |
| 2016/0370605 | A1 * | 12/2016 | Ain-Kedem | G02B 27/0172 |
| 2017/0103440 | A1 * | 4/2017 | Xing | H04W 4/90 |

OTHER PUBLICATIONS

International Search Report and Written Opinion dated Dec. 18, 2015 re PCT/US2015/051168.

* cited by examiner

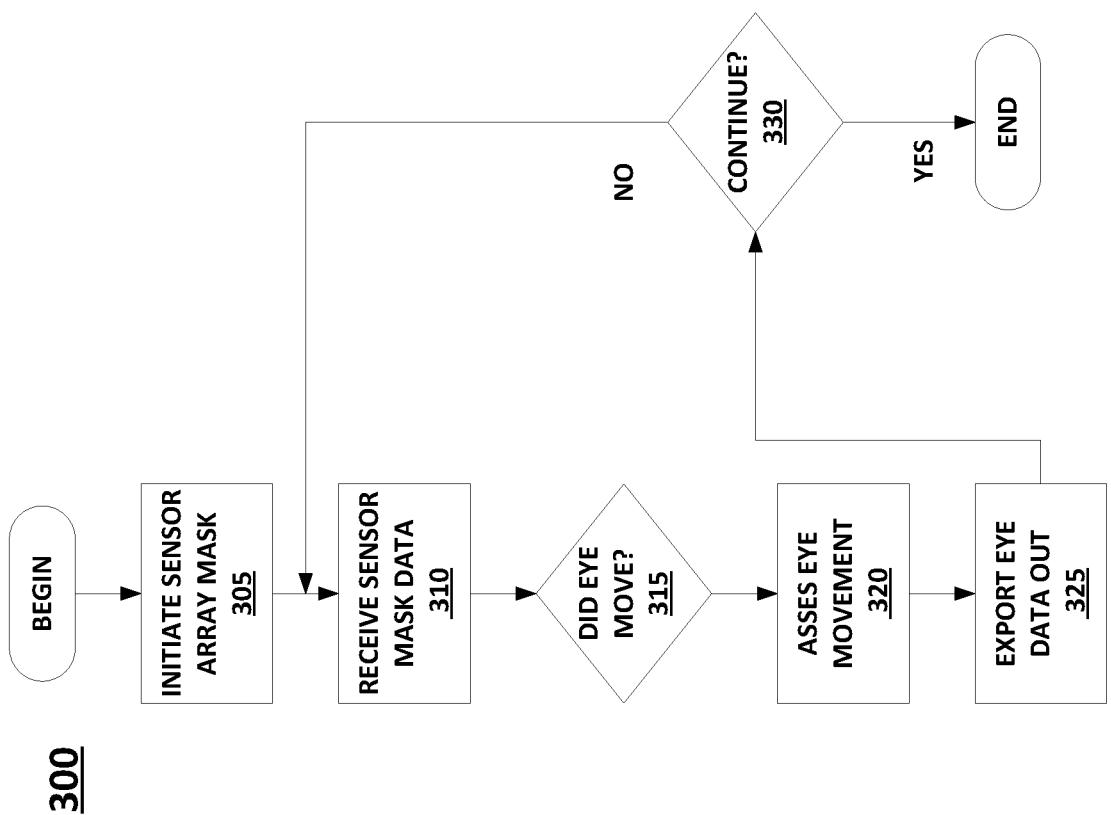

WEARABLE IN-VEHICLE EYE GAZE DETECTION

CROSS-REFERENCE TO RELATED APPLICATIONS

This patent application is filed under 35 U.S.C. § 371 as a national stage of, and as such claims priority to, International Patent Application No. PCT/US2015/051168, filed on Sep. 21, 2015, the foregoing application is incorporated herein by reference in its entirety.

BACKGROUND

A determination concerning whether a vehicle driver is distracted can sometimes be made by detecting whether the driver is looking outside at the road, or instead at passengers, the car radio, etc. Unfortunately, driver gaze monitoring systems are often expensive, unwieldy, complicated to use and bulky. Such monitoring systems can also restrict a driver's freedom of movement and/or may interfere with operation of the vehicle.

DRAWINGS

FIG. 3 is a diagram of an exemplary process for detecting the gaze of the operator wearing the mask with the sensors.

DESCRIPTION

Introduction

Figure 1:
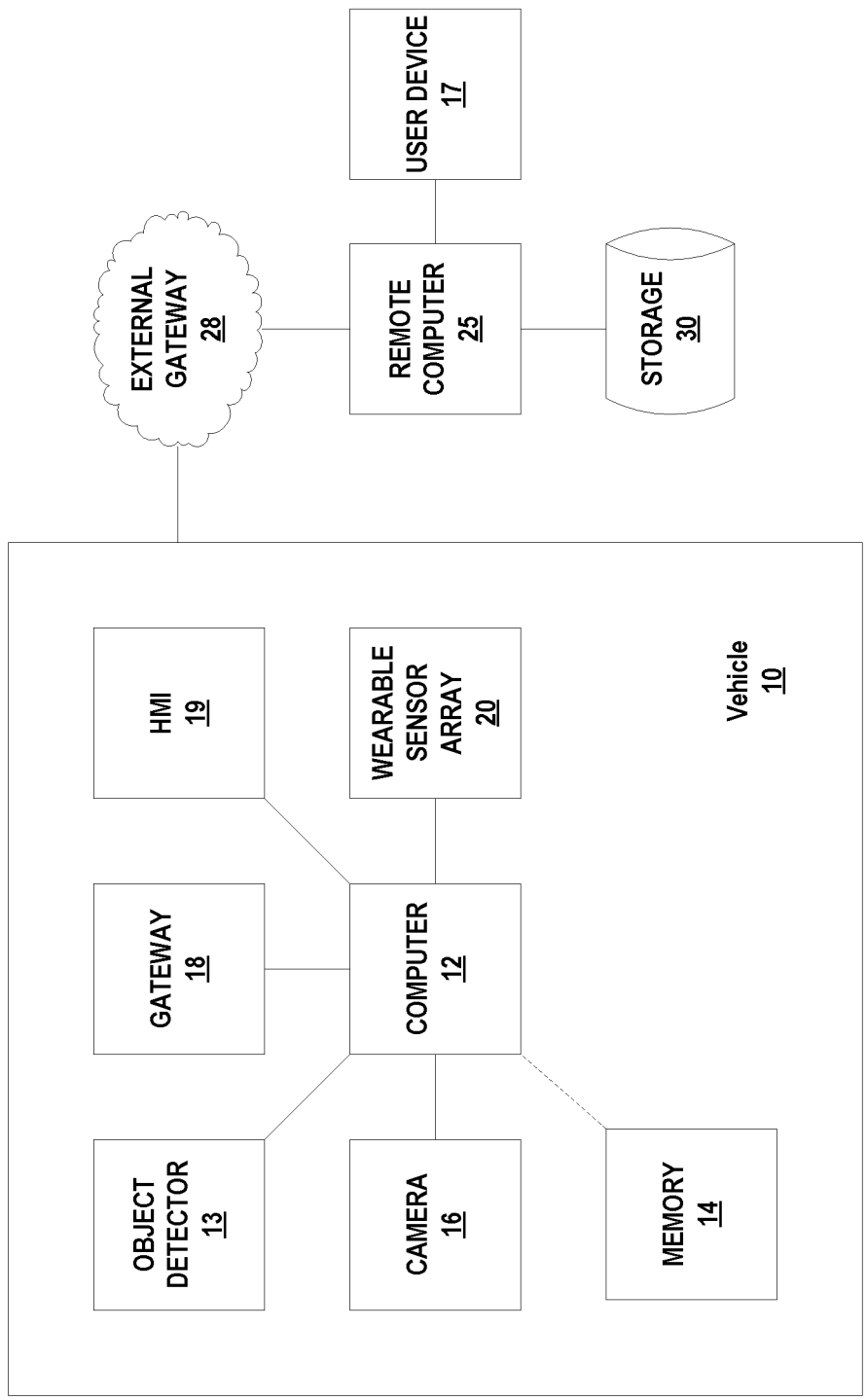
FIG. 1 is a block diagram of an exemplary wearable in-vehicle eye gaze detection system.

FIG. 1 is a block diagram of an exemplary wearable in-vehicle eye detection system 100. A vehicle 10 includes a computer 12 that receives data from a wearable sensor array face mask 20 (see FIG. 2) that is worn by an operator of the vehicle 10. The wearable sensor array face mask 20 typically includes ocular muscle motion sensors or the like, which are placed about an eye to receive electric signals of the ocular muscles, such as is known for various uses, including making measurements that may be used to determine an eye's direction of gaze. The computer 10 uses the data from the wearable sensor array face mask 20 to determine a direction of a vehicle operator's gaze, e.g., whether the operator's gaze is directed to a road or somewhere else. The computer 12 may further analyze the operator's gaze based on a road image from a camera 16 to detect a hazard of which the operator may be unaware. Further, the computer 12 may alert the operator and/or make adjustments to vehicle 10 operations based on a possible collision, e.g., with a road hazard.

Exemplary System Elements

The vehicle 10 includes a vehicle computer 12 that in turn includes a processor and a memory, the memory including one or more forms of computer-readable media, and storing instructions executable by the processor for performing various operations, i.e., programming, including as disclosed herein. For example, the computer 12 generally includes, and is capable of executing, instructions to receive data from a wearable sensor array face mask 20 to determine a gaze direction of a wearer.

The computer 12 is configured for communicating with one or more remote computer 25 and/or one or more mobile user devices 17, via a gateway 18, which, as described below, may include various wired and/or wireless networking technologies, e.g., cellular, Bluetooth, wired and/or wireless packet networks, etc. Further, the computer 12 generally includes instructions for receiving data, e.g., from the sensor array face mask 20 and/or the human machine interface (HMI) 19, which may be one or more of an interactive voice response (IVR) system, a graphical user interface (GUI) including a touchscreen or the like, etc. The computer 12 may also be connected to an external memory 14 for additional storage requirements.

The computer 12, which collects and stores data obtained from the mask 20, can send the data to a remote server 25 via an external gateway 28, which may be one or more computer servers, each generally including at least one processor and at least one memory, the memory storing instructions executable by the processor, including instructions for carrying out various steps and processes described herein. In general, the server 25 may be used for a variety of purposes, e.g., interacting with a vehicle 10 navigational system, providing data used for suggesting a vehicle 10 route and/or attributes thereof, etc. The server 25 may include or be communicatively coupled to a data store 30 for storing data such as driver fatigue information, potential waypoints for a rest stop, etc. Thus, one possible operation of the server 25 in the system 100 is to receive an indication from the vehicle 10 computer 12 via the gateway 18 that a vehicle 10 operator's eye gaze indicates the operator could need a rest break, and then for a vehicle navigation system to suggest waypoints to accommodate the possible need of the vehicle 10 operator.

A user device 17, typically a mobile device carried or worn by a user, may be any one of a variety of computing devices including a processor and a memory, as well as communication capabilities. For example, the user device 17 may be a portable computer, tablet computer, a smart phone, etc. that includes capabilities for wireless communications using IEEE 802.11, Bluetooth, and/or cellular communications protocols. Further, the user device 17 may use such communication capabilities to communicate via the gateway 18 including with a vehicle computer 12. A user device 17 could communicate with a vehicle 10 computer 12 the other mechanisms, such as a network in the vehicle 10, —known protocols such as Bluetooth, etc. Accordingly, a user device 17 may be used to carry out some or all operations herein ascribed to the computer 12, e.g., receiving data from the sensor array face mask 20, making a determination of the operator's gaze direction, and providing the determination via a user interface of the user device 17. Further, a user device 17 could be used to supplement and/or replace the HMI 19 of the computer 12.

Figure 2A:
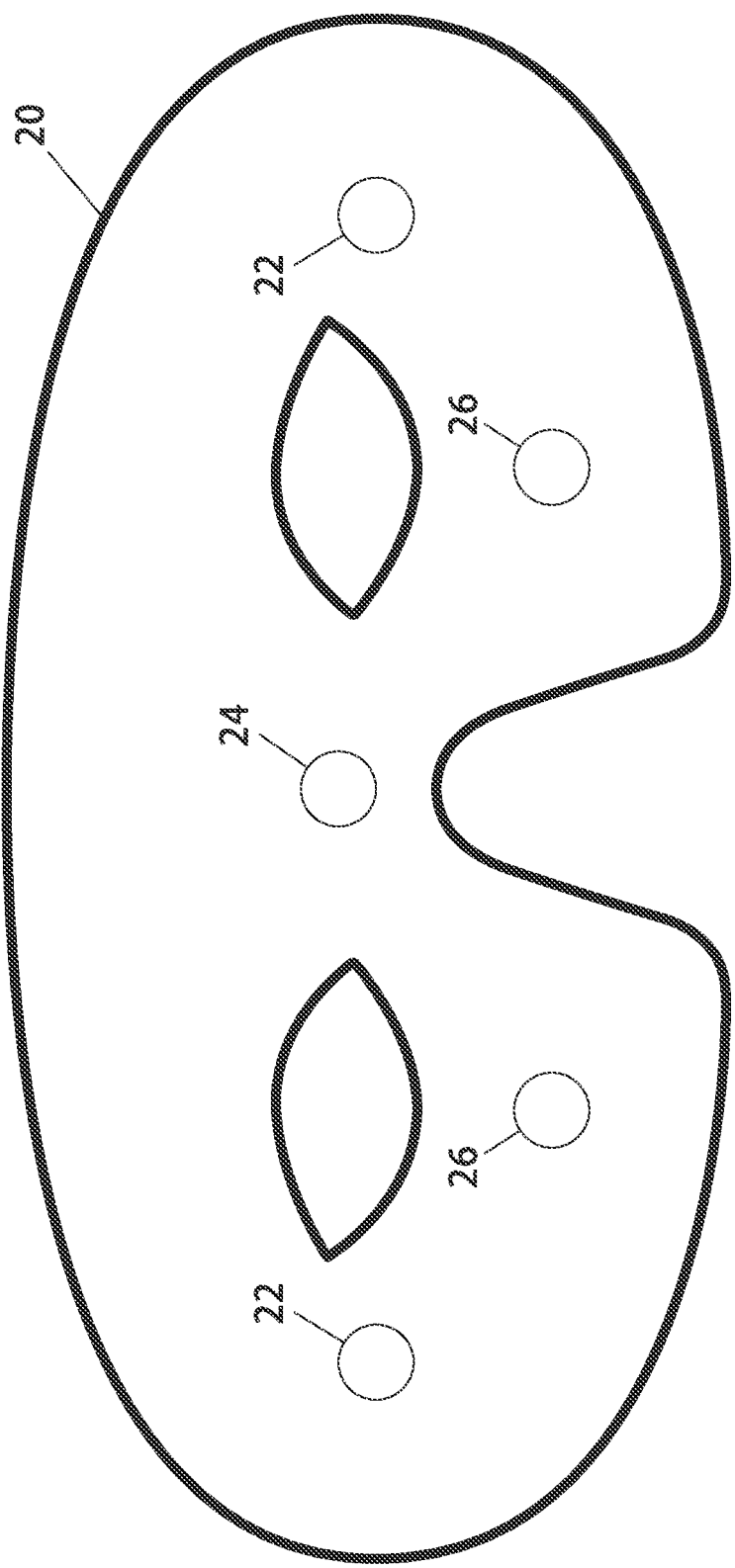
FIG. 2A is a view of a mask to be worn near the eyes of an operator showing the eye movement detection sensors in the system of FIG. 1.

A vehicle 10 operator may wear the wearable sensor array face mask 20, illustrated in FIG. 2A. The mask 20 is generally affixed to the operator so as to rest against the operator's face, and may be worn without impeding the operator's vision. The sensor array face mask 20 typically includes a plurality of ocular muscle motion sensors 22, 24, 26, placed about the mask 20. The ocular muscle motion sensor placement can include a lateral canthi motion sensor 22, an inner canthus motion sensor 24 and a maxillary motion sensor 26.

There are six extraocular muscles which act to turn or rotate the eye about its vertical, horizontal and its anterior-posterior axes. A superior oblique (SO) muscle primarily rotates the top of the eye toward the nose, downward and outward. A superior rectus (SR) muscle moves the eye upward, along a vertical meridian and rotates the top of the eye towards the nose and moves the eye inwards. A medial rectus (MR) muscle moves the eye along a horizontal meridian towards the nose. A lateral rectus (LR) muscle moves the eye along the horizontal meridian away from the nose. An inferior oblique (IO) muscle rotates the top of the eye away from the nose and also moves the eye upward and outward. An inferior rectus (IR) muscle moves the eye downwards along the vertical meridian and also rotates the top of the eye away from the nose and moves the eye inwards.

Figure 2B:
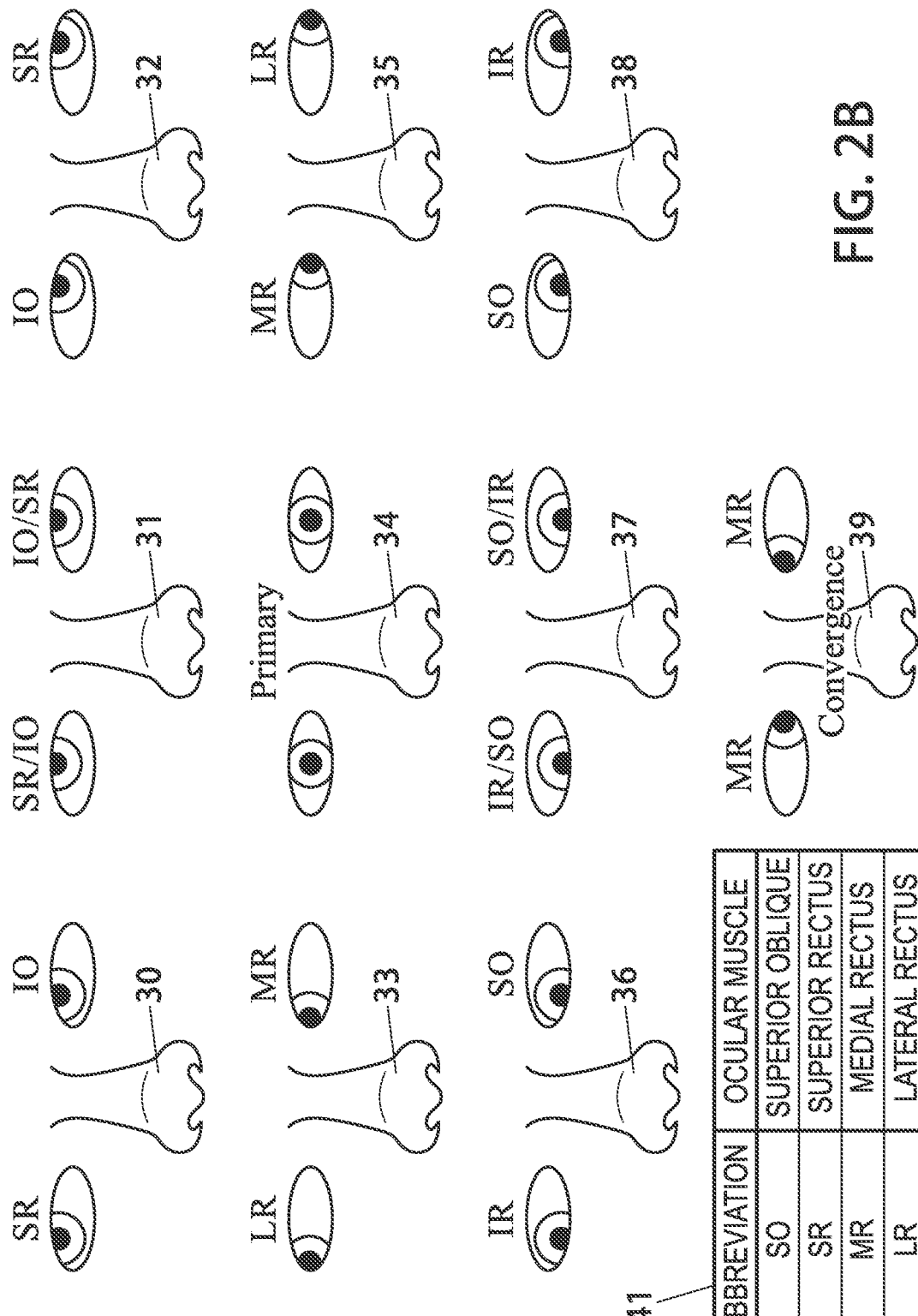
FIG. 2B illustrates the ten positions of gaze which allow comparisons of the horizontal, vertical, and diagonal ocular movements.

FIG. 2B illustrates the ten positions of gaze which allow comparisons of the horizontal, vertical, and diagonal ocular movements produced by the six extraocular muscles when both eyes and multiple muscles are working together. In an example of an up to the right gaze 30 and with reference to muscle table 41, the SR, or the superior rectus, muscle in a right eye and the IO, or the inferior oblique, —muscle in a left eye are contracting, while the other eye muscles are in a quiescent state. Muscle contraction is the activation of tension-generating sites within muscle fibers. The termination of muscle contraction is followed by muscle relaxation or quiescent state, which is a return of the muscle fibers to their low tension-generating state. The sensors 22, 24, 26 (FIG. 2A) can detect when the muscle is contracting and when the muscle is in the quiescent state. In another example, a down and to the left gaze 38 contracts the SO muscle of the right eye and the IR muscle of the left eye. A convergence 39 occurs when both right and left eye MR muscles contract.

The actions of the six muscles responsible for eye movement depend on the position of the eye at the time of muscle contraction. Four of the muscles control the movement of the eye in the four cardinal directions or up, down, left and right, while the remaining two muscles control the adjustments involved in counteracting head movement. The visual system in the brain is too slow to process information if the images are moving across a retina at more than a few degrees per second. For example, to be able to see while a person is moving, the brain must compensate for the motion of the head by turning the eyes. The eyes must follow a target as only a small portion of the eye called the fovea provides sharp vision. Since eye movements are generally fast and precise and can be voluntarily controlled, most eye movements can be accomplished without conscious effort.

The sensors 22, 24, 26 can be wirelessly connected to the vehicle 10 computer 12 or the sensors 22, 24, 26 can be directly connected to the mask 20, which can be wired into the vehicle 10 computer 12 directly and/or can communicate with the computer 12 via one or more of various wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks (e.g., using Bluetooth, IEEE 802.11, etc.), local area networks (LAN), and/or wide area networks (WAN), including the Internet, providing data communication services.

The sensor array mask 20 can be sized to accommodate the face of the vehicle 10 operator. The mask 20 can be a type of coated paper, but may, alternatively or additionally, be made of a cloth material or a plastic material. The sensor array face mask 20 can be held to the face by a Velcro strap which goes around the operator's head and/or the sensor array face mask 20 can have an adhesive applied to a first surface, i.e., a skin contacting surface. The adhesive can be an acrylate, including methacrylates and epoxy diacrylates, which are also known as vinyl resins.

A camera 16 and an object detector 13 can be placed on the vehicle 10 to detect objects in front of the vehicle 10 by sending images and/or detection information to the computer 12. The object detector 13 can be any of many types, such as LIDAR, RADAR, ultrasound, SONAR, etc. The computer 12, using gaze information could determine whether the operator's focus was outside of the vehicle 10, and/or whether the operator sees a roadway hazard. If the operator is determined to be distracted, e.g., is looking away from the roadway hazard, the computer 12 can then send an alert to the operator. The alert can be sent to the HMI 19, the user device 17, or to any other attention getting device.

Exemplary Process Flows

FIG. 3 is a diagram of an exemplary process 300 for determining a current eye gaze direction of a vehicle operator.

The process 300 begins in a block 305, in which the computer 12 initiates measurements by the sensor array face mask 20. For example, a user could provide input from a user device 17 to initiate measurements from ocular muscle motion sensors 22, 24, 26 in the sensor array face mask 20, e.g., from a smart phone app or the like. The computer 12 could detect the sensor array face mask 20 and a type and number of sensors 22, 24, 26. Further, the block 305 could include providing an identification of the subject operator to the computer 12 and/or receiving input concerning and/or retrieving parameters relating to the subject operator, such parameters provided for greater accuracy in assessing eye gaze direction as described in more detail below.

Next, in a block 310, the computer 12 receives data from the sensor array face mask 20, e.g., measurements from sensors 22, 24, 26, that, as described above, can be used as indicia of an eye location and/or direction of gaze of a vehicle occupant.

Next, in a block 315, the computer 12 determines a location change of the occupant's eye is detected, e.g., a direction of gaze has changed. Further, upon determining a direction of gaze of a user's eyes, the computer 12 may send eye movement and/or location data to a user device 17, to provide a current gaze direction of the eye. For example, a current gaze direction can include a direction and a distance of eye movement.

Next, in a block 320, the computer 12 assesses the operator's eye movements and determines the operator's current gaze direction. For example, the computer 12 may use an operator attentiveness model or other known models and/or equations to determine a gaze direction of the operator. The operator attentiveness model may use such parameters as the subject operator's age, gender, medications, height, and/or weight. Such parameters may be provided to the vehicle computer 12, e.g., according to user input via the HMI 19 and/or a user device 17, and may be stored in the computer 12 memory. Additionally, or alternatively, such parameters for a subject operator could be stored in the server 25 data store 30, and could be retrieved by the computer 12 according to an identifier for the subject operator. Whether stored locally on the computer 12 or remotely at the server 25 such parameters could be used to dynamically improve prediction performance of a stochastic model.

Next, in a block 325, the computer 12 may provide the assessment to the HMI 19, a user device 17, etc. The computer 12 may also provide the assessment to the server 25, where may be stored in the data store 30. A user, e.g., via the computer 12 or a user device 17, could provide further input to be provided to the server 25 to allow for adaptive learning and refinement with respect to a particular subject operator or calculations of the current gaze more generally. Accordingly, the computer 12 may receive updates of one or more models, e.g., a plurality of models corresponding to different parameters, from the server 25, and/or may be programmed to make such updates. Further, as mentioned above, the assessment of the current gaze of the subject operator made in the block 320 may be used as a basis for vehicle 10 operations. For example, if the assessment of the operator indicates that the operator appears to be drowsy, the vehicle computer 12 may request that the vehicle 10 navigation system provide a route, or modify an existing route, to indicate one or more waypoints having a rest area.

Next, in a block 330, the computer 12 determines whether the process 300 is to continue. For example, a user could provide input stopping measurements from the sensor array face mask 20, the computer 12 could detect that the sensor array face mask 20 has been removed from the subject operator, etc. alternatively or additionally, the process 300 may not continue if the vehicle 10, including the computer 12, is powered off and/or stopped. In any case, if the process 300 continues, the block 310 is executed. Otherwise, the process 300 ends following the block 330.

Figure 4:
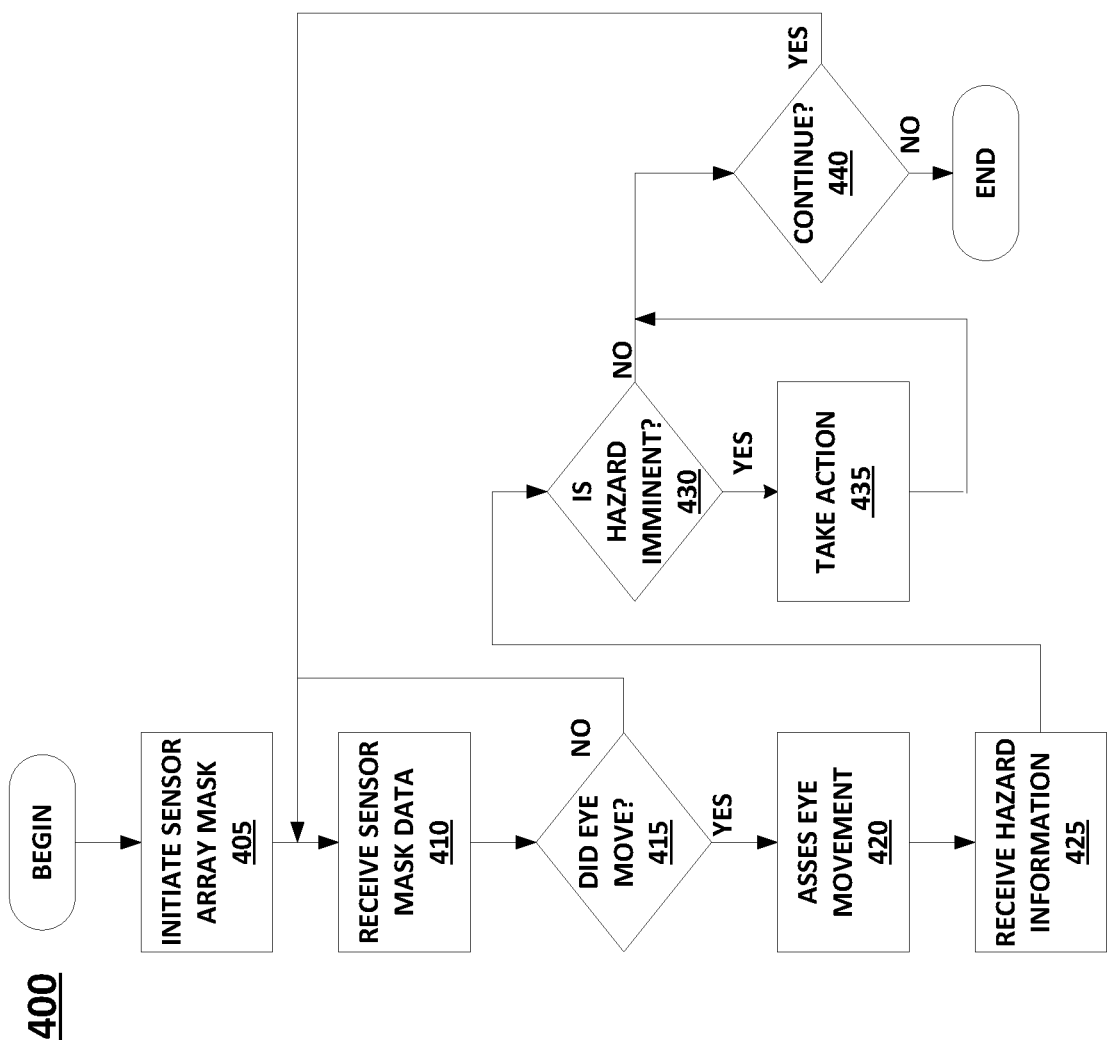
FIG. 4 is a diagram of another exemplary process for detecting the gaze of the operator wearing the mask with the sensors.

FIG. 4 is a diagram of another exemplary process 400 for determining a current eye gaze in a vehicle operator and alerting the operator whose gaze is not where it should be. The process 400 begins in a block 405, which is similar to the block 305. Further, a block 410, following the block 405, is likewise similar to the block 310 described above.

In a block 420, following the block 410, the computer 12, in a manner similar to that described above with respect to the block 320, makes an assessment of the current gaze of the subject operator.

Next, in a block 425, the computer 12 receives information regarding any potential hazards. For example, an image from the camera 17 can be digitally processed to determine if any objects are in front of the vehicle 10. Additionally or alternatively, the object detector 13 can indicate to the computer 12 potential hazards.

In a block 430, the computer 12 determines if a hazard is imminent, e.g., present and presenting a danger to the vehicle 10. The presence or absence of a road hazard could be determined by using vehicle 10 sensor data to determine a potential obstacle, determine a distance of the obstacle, a likelihood that the vehicle 10 will intersect the obstacle, etc. For example, the computer can determine if the eye gaze is not in the direction of an actual or potential hazard, such as a stationary object, a moving object or a principal other vehicle (POV), which is likely to come into the current or potential direction of movement and present a danger to the vehicle 10. In another example, the computer 12 can also determine a trajectory of eye gaze movement and assess if a potential or actual hazard will likely be noticed in a timely manner. If so, a block 435 is executed next, else a block 440 is executed.

In the block 435, the computer 12 actuates one or more operations in the vehicle 10 based on the detected hazard, alerts the operator that there is a hazard outside of the vehicle 10 with a warning. For example, the warning can be an audible tone played through the HMI 19 and/or the computer 12 can vibrate the steering wheel. Further for example, the operations could include at least one of actuating a vehicle 10 throttle, steering, and brakes to avoid a hazard. For example, on determining an imminent hazard, and that an operator's attention falls below an attentiveness threshold, the computer 12 could be programmed to apply the vehicle 10 brakes and/or control the vehicle 10 steering, e.g., by providing instructions to an electronic control unit in a known manner, to avoid the hazard.

In a block 440, which may follow the blocks 430, 435, in a manner similar to that described above with respect to the block 330, it is determined whether the process 400 continues. If so, then the block 410 is executed next. Otherwise, the process 400 ends.

Figure 5:
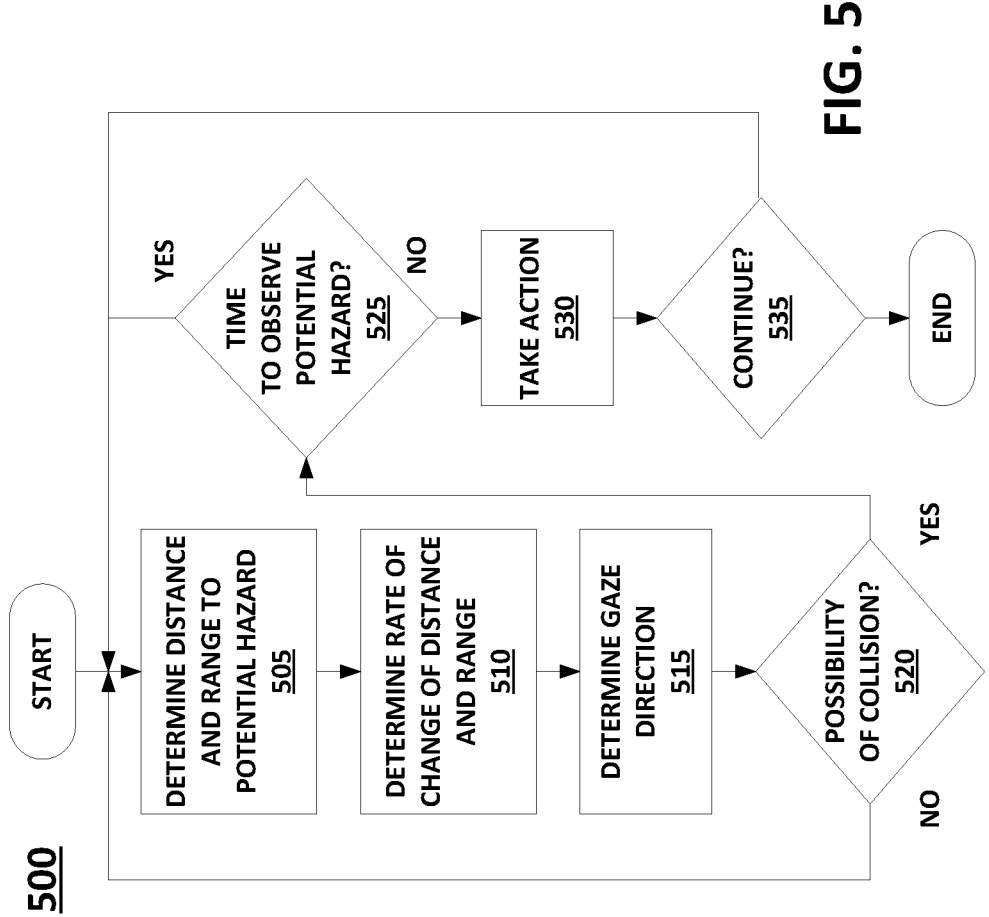
FIG. 5 is a diagram of another exemplary process for detecting the gaze of the operator wearing the mask with sensors.

FIG. 5 is a diagram of another exemplary process 500 for determining a current eye gaze in a vehicle operator and alerting the operator whose gaze is not where it should be.

The process 500 begins in a block 505, in which the computer 12 receives information regarding any potential hazards and determines a distance and a range to the potential hazard. For example, the image from the camera 17 can be digitally processed to determine the distance and a bearing to any objects that are in front of the vehicle 10. Additionally or alternatively, the object detector 13 can indicate the distance and bearing to the computer 12 of potential hazards.

Next in a block 510, the computer determines a rate of change of the distance and bearing to the potential hazard. For example, the potential hazard may be ten meters closer to the vehicle 10 than a previous determination.

Next in a block 515, the gaze direction is obtained, which can be attained from a process likewise similar to the blocks of the process 300.

Next in a block 520, the computer 12 determines if there is a possibility of collision. For example, the computer would use such factors as the velocity of the vehicle 10, the distance and bearing to the potential hazard, and the potential hazard's movement, etc. If there is not a possibility of collision, such as when the potential hazard moves from the path of the vehicle 10, the process returns to the block 505, else the process continues in a block 525.

In the block 525, the computer 12 determines if there is time for the vehicle 10 operator to observe the potential hazard without intervention by the computer 12. The determination may be based upon time to travel to the potential hazard. If the travel time is substantially large, the process returns to the block 505, else the process 500 continues in a block 530. For example, the potential hazard is 50 meters in front of the vehicle 10, at ten kilometers per hour it would take approximately 18 seconds for the vehicle 10 to reach the potential hazard. Alternatively, if the vehicle 10 was traveling at 100 kilometers per hour, the travel time would be less than two seconds.

In the block 530, the computer 12 actuates one or more operations in the vehicle 10 based on the detected hazard, and alerts the operator that there is a hazard outside of the vehicle 10 with a warning, which is similar to the block 435 of the process 400.

In a block 535, in a manner similar to that described above with respect to the block 330, it is determined whether the process 500 continues. If so, then the block 505 is executed next. Otherwise, the process 500 ends.

CONCLUSION

As used herein, the adverb "substantially" means that a shape, structure, measurement, quantity, time, etc. may deviate from an exact described geometry, distance, measurement, quantity, time, etc., because of imperfections in materials, machining, manufacturing, etc.

The term "exemplary" is used herein in the sense of signifying an example, e.g., a reference to an "exemplary widget" should be read as simply referring to an example of a widget.

Computing devices such as those discussed herein generally each include instructions executable by one or more computing devices such as those identified above, and for carrying out blocks or steps of processes described above. For example, process blocks discussed above are embodied as computer-executable instructions.

Computer-executable instructions may be compiled or interpreted from computer programs created using a variety of programming languages and/or technologies, including, without limitation, and either alone or in combination, Java™, C, C++, C #, Python, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system, comprising:
   one or more sensors included in an apparatus wearable by a vehicle operator to measure ocular muscle movement; and
   a computer that includes a processor and a memory, the memory storing instructions executable by the computer such that the computer is programmed to:
   receive data indicating ocular muscle movement from the wearable sensor;
   determine, using the measurement, a gaze direction of the operator;
   use the gaze direction to determine a level of operator attentiveness;
   actuate a vehicle operation if the level of operator attentiveness based on the gaze direction is below a predetermined threshold;
   determine a roadway hazard in a path of the vehicle from vehicle sensor data;
   determine a lack of attention to the roadway hazard based on a determination that the gaze direction has changed away from a direction of the roadway hazard; and
   warn the operator upon determining the lack of attention to the roadway hazard.

2. The system of claim 1, wherein the computer is further programmed to retrieve, from the memory, a parameter concerning the gaze direction, and to use the parameter in determining the level of operator attentiveness.

3. The system of claim 1, wherein the vehicle operation includes at least one of actuating a throttle, actuating a steering mechanism, and actuating brakes.

4. The system of claim 1, wherein the computer is further programmed to provide the gaze direction to at least one of a human-machine interface of the in-vehicle computer and a mobile user device.

5. The system of claim 1, wherein the computer is further programmed to provide the gaze direction to a remote server.

6. The system of claim 1, wherein the computer is further programmed to determine operator fatigue based on the gaze direction, and to determine a waypoint for the vehicle when operator fatigue indicates drowsiness.

7. The system of claim 1, wherein ocular muscle movement is contraction of at least one muscle in each eye while the other muscles in each eye are relaxed.

8. The system of claim 7, wherein the instructions further include instructions to determine the gaze direction based on the one or more muscles in each eye that are contracted.

9. A method, comprising:
   receiving from one or more sensors included in an apparatus wearable by a vehicle operator to measure ocular muscle movement; and
   determining, using the measurement, a gaze direction of the operator;
   using the gaze direction to determine a level of operator attentiveness;
   actuating a vehicle operation if the level of operator attentiveness based on the gaze direction is below a predetermined threshold;
   determining a roadway hazard in a path of the vehicle from vehicle sensor data;
   determining a lack of attention to the roadway hazard based on a determination that the gaze direction has changed away from a direction of the roadway hazard; and
   warning the operator upon determining the lack of attention to the roadway hazard.

10. The method of claim 9, further comprising retrieving, from the memory, a parameter concerning the gaze direction, and to use the parameter in determining the level of operator attentiveness.

11. The method of claim 9, wherein the vehicle operation includes at least one of actuating a throttle, actuating a steering mechanism, and actuating brakes.

12. The method of claim 9, further comprising providing the gaze direction to at least one of a human-machine interface of the in-vehicle computer and a mobile user device.

13. The method of claim 9, further comprising providing the gaze direction to a remote server.

14. The method of claim 9, further comprising determining operator fatigue based on the gaze direction, and determining a waypoint for the vehicle when operator fatigue indicates drowsiness.

15. The method of claim 9, wherein ocular muscle movement is contraction of at least one muscle in each eye while the other muscles in each eye are relaxed.

16. The method of claim 15, further comprising determining the gaze direction based on the one or more muscles in each eye that are contracted.

17. A system, comprising a processor; and a memory, the memory storing instructions executable by the processor to:
   receive data from one or more sensors included in an apparatus wearable by a vehicle operator to measure ocular muscle movement; and
   determine, using the measurement, a gaze direction of the operator;
   use the gaze direction to determine a level of operator attentiveness;
   actuate a vehicle operation if the level of operator attentiveness based on the gaze direction is below a predetermined threshold;
   determine a roadway hazard in a path of the vehicle from vehicle sensor data;
   determine a lack of attention to the roadway hazard based on a determination that the gaze direction has changed away from a direction of the roadway hazard; and
   warn the operator upon determining the lack of attention to the roadway hazard.

18. The system of claim 17, wherein the processor is further programmed to retrieve, from the memory, a parameter concerning the gaze direction, and to use the parameter in determining the level of operator attentiveness.

19. The system of claim 17, wherein the processor is further programmed to determine operator fatigue based on the gaze direction, and to determine a waypoint for the vehicle when operator fatigue indicates drowsiness.

20. The system of claim 17, wherein ocular muscle movement is contraction of at least one muscle in each eye while the other muscles in each eye are relaxed.

* * * * *